(12) United States Patent
Zlotnik et al.

(10) Patent No.: US 8,178,048 B2
(45) Date of Patent: May 15, 2012

(54) FIXTURE FOR DISPERSION OF AROMATIC VAPORS

(75) Inventors: Arnold H. Zlotnik, Pittsburgh, PA (US); Raymond Czapko, Pittsburgh, PA (US)

(73) Assignee: Pestco, Inc., Pittsburgh, PA (US)

( * ) Notice: Subject to any disclaimer, the term of this patent is extended or adjusted under 35 U.S.C. 154(b) by 496 days.

(21) Appl. No.: 12/381,050

(22) Filed: Mar. 6, 2009

(65) Prior Publication Data

US 2009/0274588 A1    Nov. 5, 2009

Related U.S. Application Data

(60) Provisional application No. 61/126,360, filed on May 2, 2008.

(51) Int. Cl.
| A61L 9/00 | (2006.01) |
| A62B 7/08 | (2006.01) |
| A24F 25/00 | (2006.01) |
| B65H 3/44 | (2006.01) |
| B01D 47/00 | (2006.01) |
| B01D 50/00 | (2006.01) |
| B67D 5/00 | (2006.01) |
| B67D 5/06 | (2006.01) |

(52) U.S. Cl. .............. 422/124; 422/5; 422/123; 239/34; 239/57; 239/302; 221/93; 261/DIG. 65; 261/26; 261/142; 261/DIG. 88; 261/104; 261/75; 261/DIG. 17; 55/274; 55/279; 55/385.1; 55/486; 55/521; 96/222; 96/243; 222/3; 222/180; 222/187

(58) Field of Classification Search ...... 422/5, 123–124; 239/34, 57, 302; 221/93; 261/DIG. 65, 26, 261/142, DIG. 88, 104, 75, DIG. 17; 55/274, 279, 385.1, 486, 521; 96/222, 243; 222/3, 180, 187

See application file for complete search history.

(56) References Cited

U.S. PATENT DOCUMENTS

| 4,707,338 A * | 11/1987 | Spector .......................... 422/124 |
| 4,857,240 A * | 8/1989 | Kearnes et al. .................. 261/26 |
| 5,533,705 A | 7/1996 | Zlotnik |
| 5,816,845 A | 10/1998 | Chisima |
| 6,105,916 A | 8/2000 | Zlotnik |
| 2004/0082495 A1 | 4/2004 | Maleeny |

* cited by examiner

*Primary Examiner* — Jill Warden
*Assistant Examiner* — Monzer Chorbaji
(74) *Attorney, Agent, or Firm* — Clifford A. Poff; Suzanne Kikel

(57) ABSTRACT

A dispenser fixture for dispersing aromatic vapors into a facility includes an elongated dispenser chamber bounded by end walls, one containing a motor driven fan and the other wall containing fixtures for supplying and controlling electrical current for powering the fan motor. The chamber, containing trays supporting a replaceable supply of aromatic material, presents the aromatic material to an air flow passing into apertures positioned near or in the other wall such that a carrier arm supporting the fixture orientates the fan motor to discharge air enriched with aromatic vapors in a horizontal direction into the facility. The fixture includes upstanding side walls joining the end walls, a floor wall joining the side walls and the end walls, and a top wall overlying the side and end walls for enclosing the aromatic materials in the chamber. The dispenser fixture may be made of a hard plastic or metal.

4 Claims, 11 Drawing Sheets

FIXTURE FOR DISPERSION OF AROMATIC VAPORS

CLAIM TO PRIORITY

This application claims the benefit of U.S. Provisional Patent Application No. 61/126,360 filed May 2, 2008, the contents of which are hereby incorporated into this application.

BACKGROUND OF THE INVENTION

1. Field of the Invention

The present invention relates to a dispenser fixture for aromatic materials. More particularly, the present invention relates to a dispenser chamber having a tray for presenting a supply of aromatic materials to a flow of air passing from apertures positioned near or in the end wall of a fixture for dispersing aromatic vapors in a manner that a carrier arm supporting the dispenser orientates a motor driven fan to discharge a stream of air enriched with aromatic vapors in a generally horizontal direction.

2. Description of the Prior Art

A dispenser for volatile fluid is disclosed in U.S. Pat. Nos. 5,533,705; 5,816,845; and 6,105,916. These dispensers provide a drive selectively using a large or small motor providing an air stream for generating vapor from a wick, ceramic wafers, or discs containing vaporizable deodorant and a reversible drive mounting mounted back-to-back. U.S. Pat. No. 6,957,779 discloses a framed fluid delivery device that includes a fluid delivery cartridge for the timed release delivery of a fluid. These known deodorant dispensers are commonly used and recognized by the public because of their use for dispersing fragrances in hostile environments such as restrooms where it is desirous to control the nature of the atmosphere.

A need exists for a deodorant or fragrant dispenser having a robust construction for discharging air streams within a large room such as a restaurant, coffee house and the like in a manner to produce a pleasant environment conducive to the sale of products on the premises.

A need also exists for providing a deodorant or fragrant dispenser that is designed so that it is not recognized as a traditional prior art dispenser in order to maintain the privacy of the source of the air stream.

SUMMARY OF THE INVENTION

The present invention has met these needs. The present invention provides a dispenser fixture for dispersion of aromatic vapors and includes an elongated dispenser chamber bounded by end walls, one end wall containing a fan driven by a motor and the other end wall containing fixtures for supplying and controlling electrical current to power the motor for driving the fan. The dispenser chamber contains one or more receptacles, for example rectangular trays, for presenting a supply of aromatic materials to a flow of air passing from apertures that are positioned near or in the end wall containing the fixtures such that a carrier arm supporting the dispenser fixture orientates the motor driven fan to discharge a stream of air enriched with aromatic vapors in a generally horizontal direction and out into the environment.

The elongated dispenser chamber further includes upstanding side walls joined with a floor wall containing a load bearing surface supporting at least one receptacle containing a replaceable supply of aromatic material and an inboard end wall supporting an electrical supply utility. In the embodiments of the present invention, the dispenser fixture has one or more apertures for admitting a flow of ambient air into the dispensing chamber. The elongated dispenser chamber includes an outboard end wall having an aperture aligned with an air flow path from a blower supported by the outboard end wall and connected by wiring that traverses the elongated dispenser chamber with the electrical supply utility for energizing the blower. The top wall or cover of the dispenser chamber is mounted by a hinge for pivotally fastening the top wall to one of the upstanding side walls in order to facilitate relative movement from an open position to a closed position. The top wall or cover overlies the upstanding side walls, the inboard end wall, and the outboard end wall.

The closed position of the dispenser chamber defines a condition in which ambient air supplied by the one or more apertures of the dispenser fixture is enriched with aromatic vapors in the dispenser chamber and is driven by the blower as an ambient exhaust. The open position of the dispenser chamber defines a condition in which the aromatic material supported in the receptacle or receptacles is accessible for replacement in the elongated dispenser chamber. A carrier arm has a mounting flange on a terminal end of the dispenser chamber and projects outwardly from a base adapted for attachment to a support. The mounting flange through suitable fasteners is attached to the dispenser fixture, for example the floor wall, to orientate the floor wall in a substantially horizontal direction and thus the dispenser fixture in a horizontal orientation. Additional fasteners secure the top wall or cover of the dispenser chamber to one of the upstanding side walls, to the inboard end wall and to the outboard end wall of the dispenser chamber.

It is therefore an object of the present invention to provide a dispenser fixture having a robust construction for discharging air streams within a large room such as a restaurant or a coffee house in a manner to produce a pleasant environment conducive to the sale of products on the premises.

It is a further object of the present invention to provide a dispenser fixture designed such that it is camouflaged so that it is not recognized as a traditional prior art dispenser and therefore the source of the fragrant air stream is not recognized.

These and other objects and advantages of the present invention will be better appreciated and understood when the following description is read in light of the accompanying drawings.

DETAILED DESCRIPTION OF THE INVENTION

Figure 1:
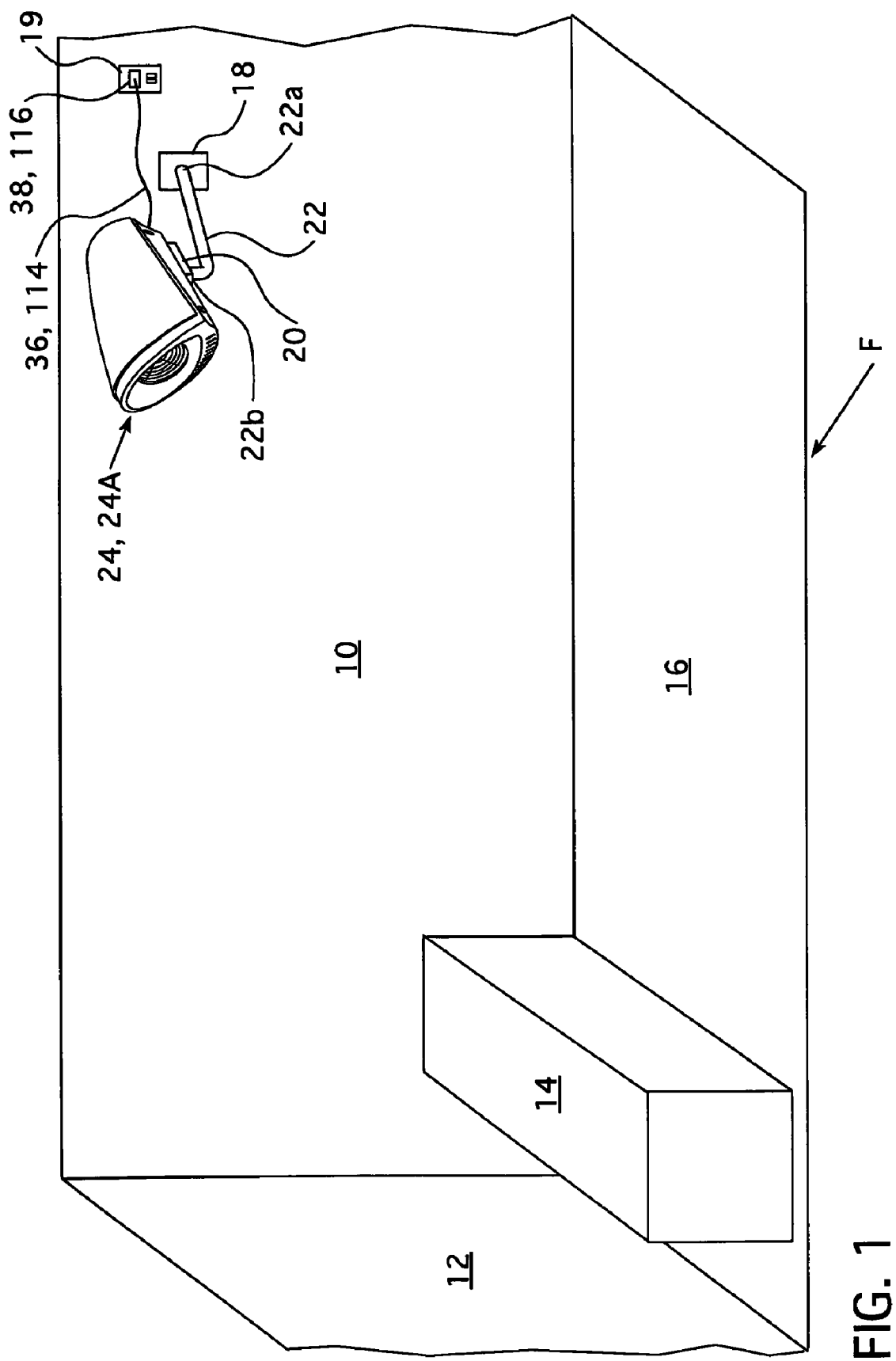
FIG. 1 is a partial isometric schematic view of a retail establishment selling products and includes a dispenser fixture for the dispersion of aromatic vapors according to the present invention.

FIG. 1 illustrates a side wall 10 and an end wall 12 of a retail establishment or facility F engaged in the sale of a commodity or product, such as coffee, at a counter 14 supported by a floor 16. A base 18 is mounted to the sidewall 10 and is adapted to be supported by side wall 10. A carrier arm 22 has a terminal end 22a which is mounted to base 18, which in turn is mounted to side wall 10, through suitable fasteners known to those skilled in the art. Carrier arm 22 further includes terminal end 22b attached to a mounting flange 20 which in turn is structured to support and be fastened through suitable fasteners to a dispenser fixture 24, 24A outwardly from side wall 10. Dispenser fixture 24, 24A is structured to disperse aromatic vapors into the facility and is orientated horizontally within the facility F via carrier arm 22.

The structure of dispenser fixture 24, 24A and its location within the facility F is such that a high velocity air stream emitted by the facility enters one end of the dispenser fixture 24, 24A, is orientated in a substantially horizontal orientation within dispenser fixture 24, 24A, and exits the other end of dispenser fixture 24, 24A for emission of aromatic vapors out into the facility. Carrier arm 22 may be pivotally mounted to base 18 for pivotal movement with dispenser fixture 24, 24A relative to side wall 10, in which instance, dispenser fixture 24, 24A preferably remains in a horizontal positioning relative to carrier arm 22. Preferably, dispenser fixture 24, 24A is an electrical device and includes an electrical supply utility 36, 114 whose outlet plug 38, 116 is inserted into an electrical socket 19 in FIG. 1, more about which is discussed herein below.

Figure 3:
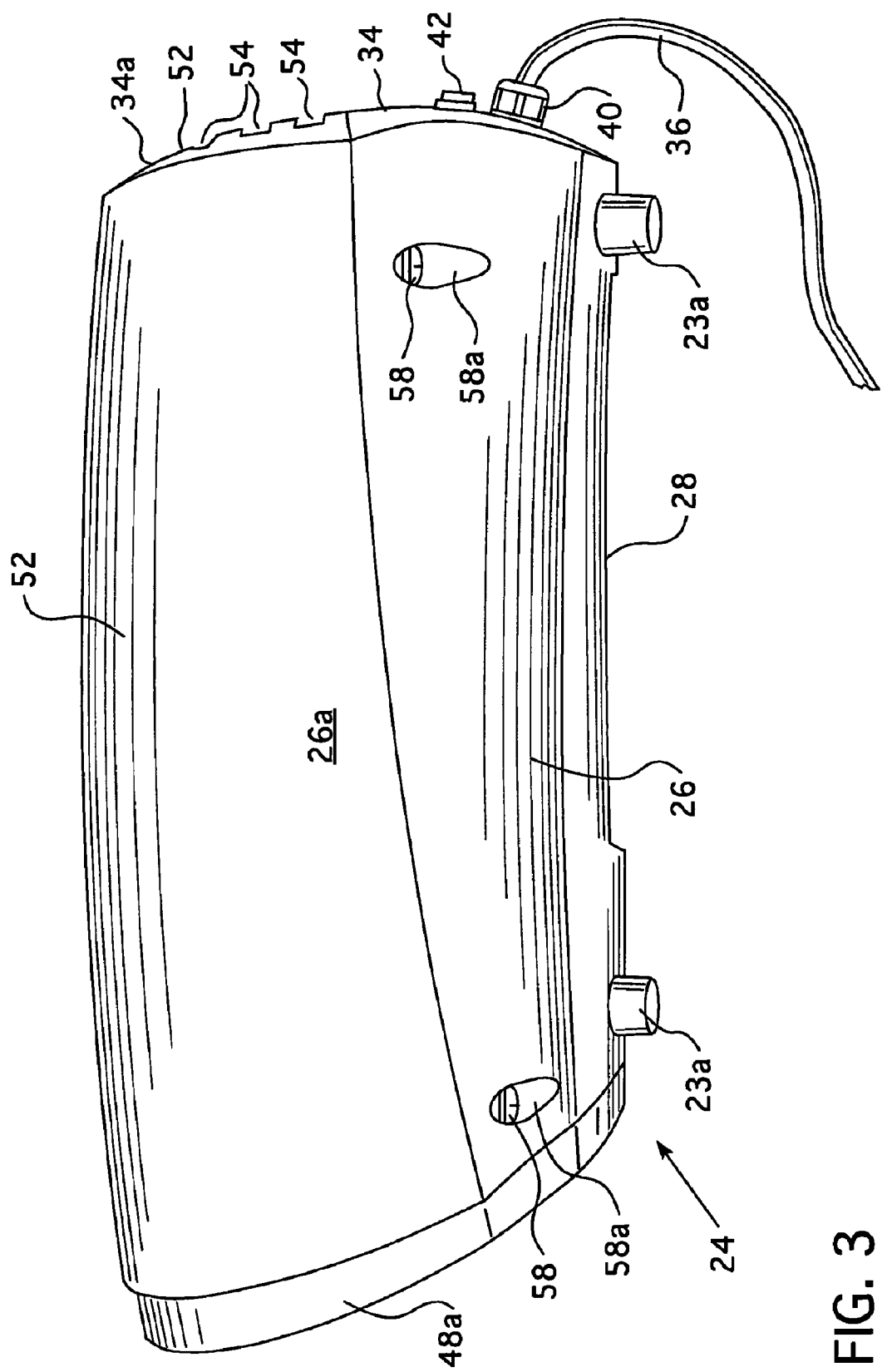
FIG. 3 is a right side elevation view of the dispenser fixture of FIG. 2.
Figure 4:
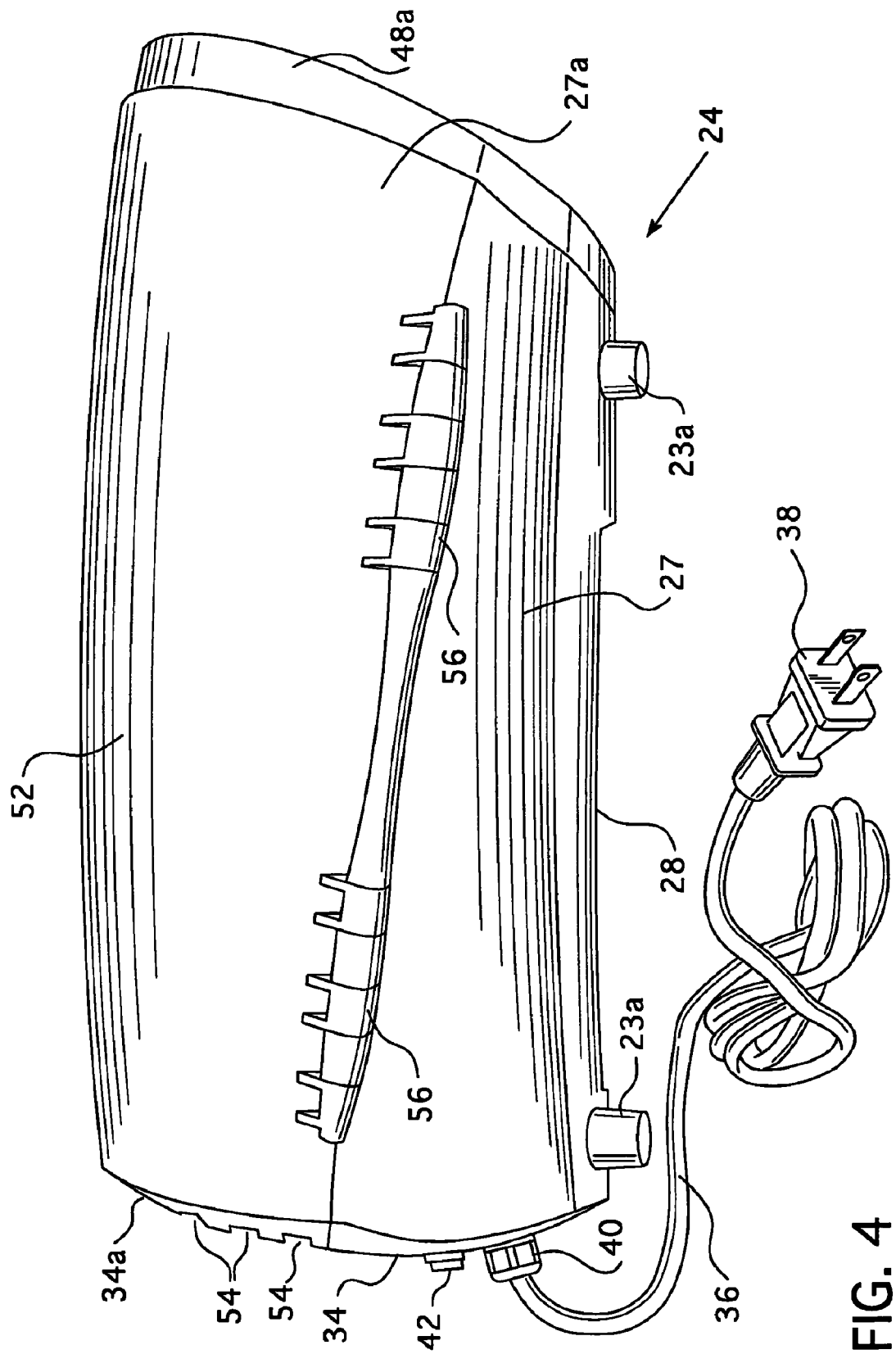
FIG. 4 is a left side elevation view of the dispenser fixture of FIG. 2.
Figure 5:
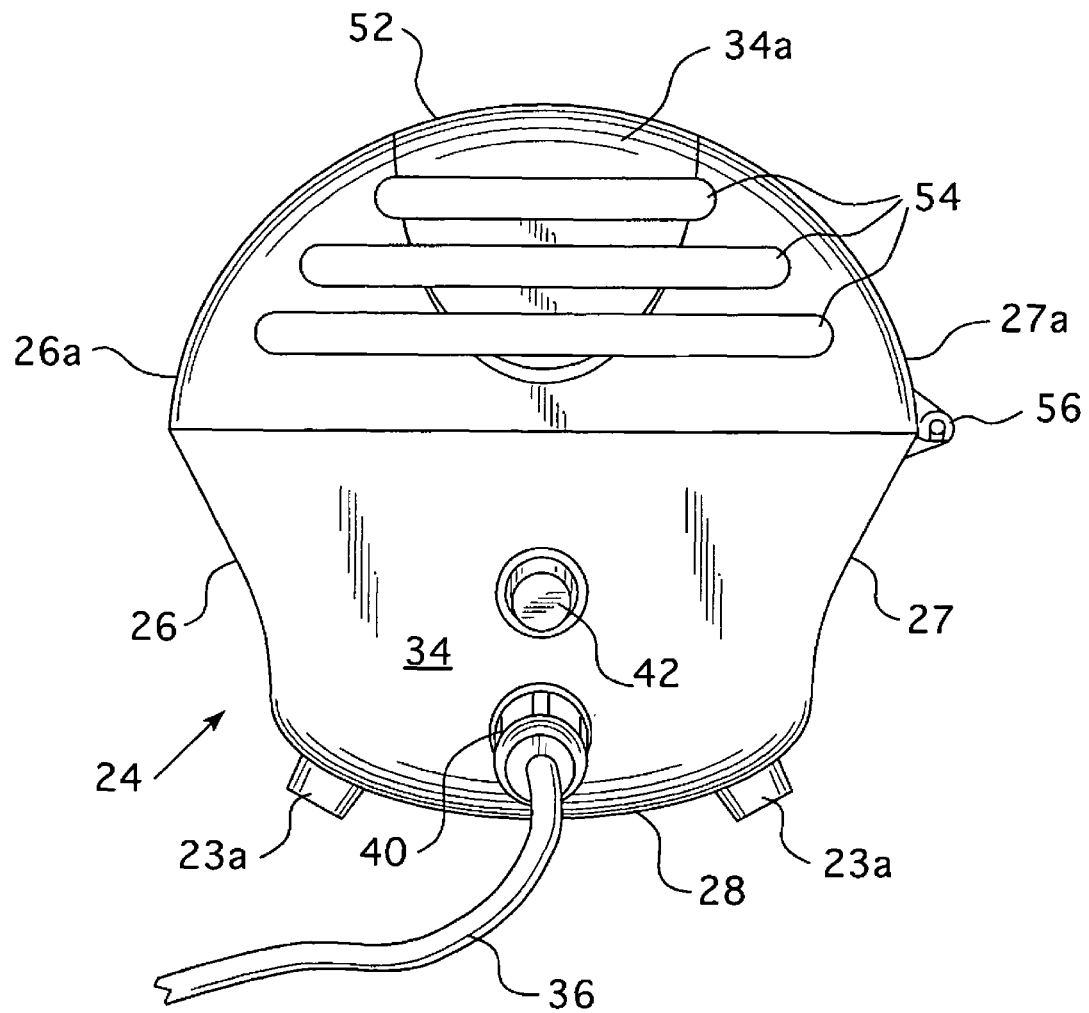
FIG. 5 is a rear elevation view of the dispenser fixture of FIG. 2.

As shown in FIGS. 2-7, a first embodiment of the present invention involves dispenser fixture 24 having several legs 23a for supporting dispenser fixture 24 on a surface. Dispenser fixture 24 further includes upstanding side walls 26 and 27 which are joined with a floor wall 28 as best shown in FIG. 5. As shown particularly in FIG. 7, floor wall 28 has a load bearing surface 30 for supporting at least one rectangular tray 32 constructed to contain a replaceable supply of aromatic material. As shown best in FIG. 6, an inboard end wall 34 supports the electrical supply utility 36 in the form of an electrical utility cable with the outlet plug 38 on its free end and a mounting fixture 40 at its entrance into the interior of dispenser fixture 24.

Figure 2:
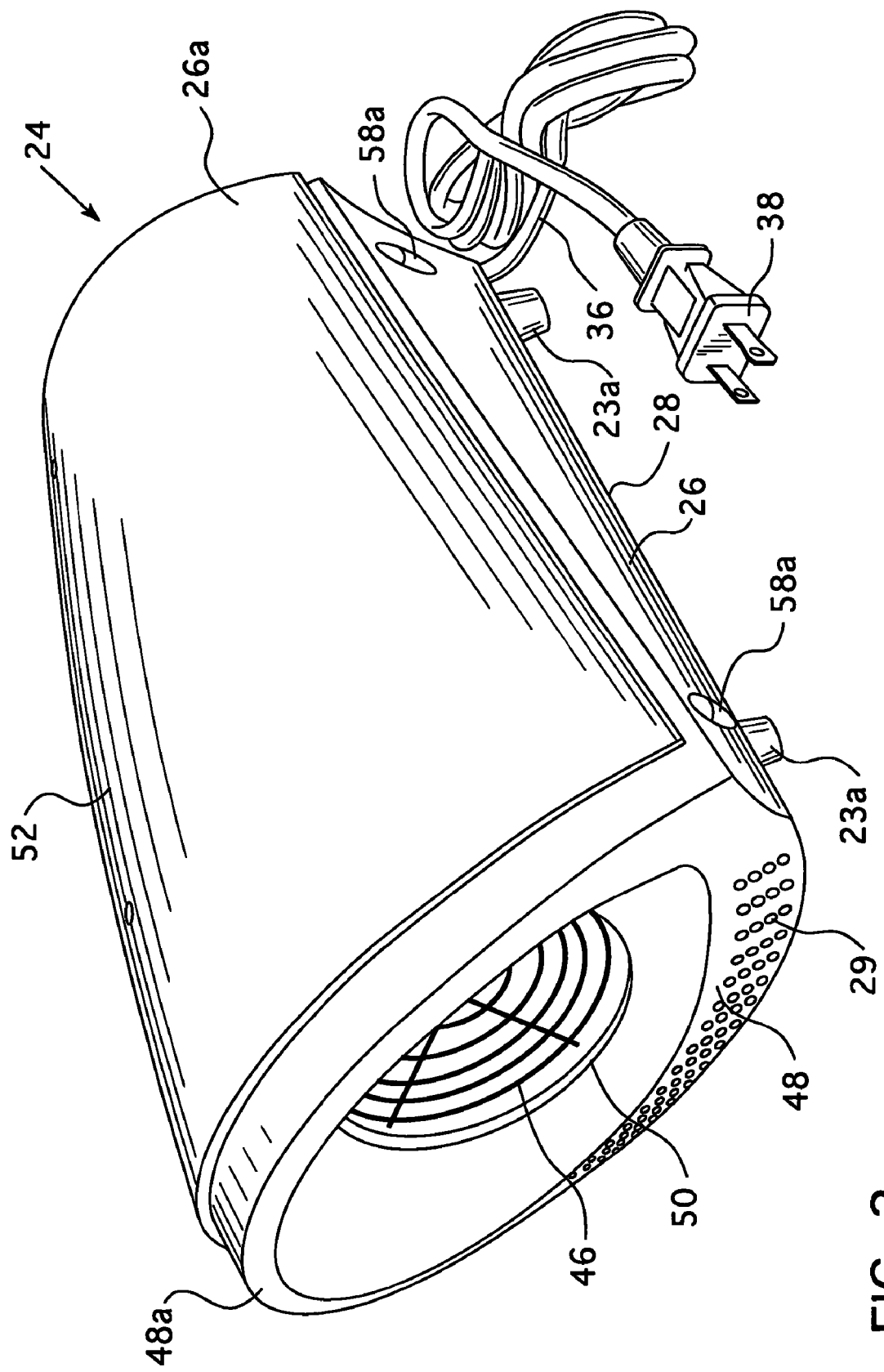
FIG. 2 is a frontal right side isometric view of a first embodiment of a dispenser fixture of the present invention.
Figure 6:
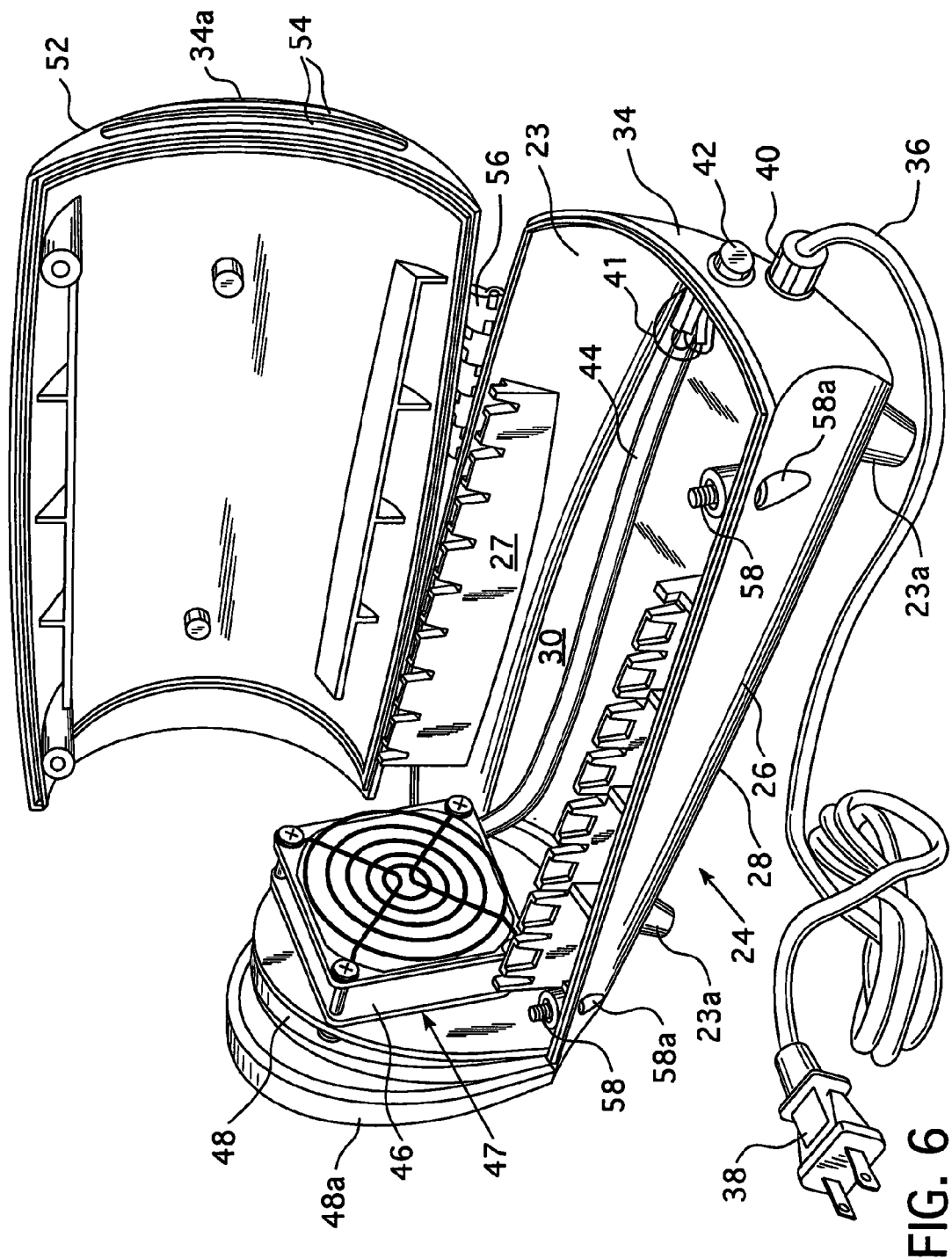
FIG. 6 is an isometric view of the dispenser fixture of FIG. 2 with the top wall or cover pivotally displaced from a closed position.

Referring particularly to FIG. 6, suitable wiring 41 is arranged within dispenser fixture 24 for electrically connecting a control switch 42 into a circuit for supplying electrical current by a feed line 44 to a blower 46, preferably, in the form of an electric motor which is mounted in a fan assembly 47. With particular reference to FIG. 6, the fan assembly 47 is mounted to an outboard end wall 48 of the dispenser fixture 24 and has an aperture 50 as shown in FIG. 2, which is aligned with an air flow path from blower 46. As best shown in FIG. 2, aperture 50 and blower 46 are located in the outboard end wall 48 of dispenser fixture 24.

Referring again to FIG. 6, feed line 44 traverses an elongated dispenser chamber 23. Referring particularly to FIGS. 2, 3, 4, and 5, dispenser chamber 23 constitutes the volume contained within inboard end wall 34, outboard end wall 48, side walls 26 and 27, floor wall 28, and a top wall or cover 52.

In the first embodiment of FIGS. 2 through 7 and as best shown in FIG. 5, an end wall extension 34a of top wall or cover 52, which is adjacent to the inboard end wall 34 when dispenser fixture 24 is closed, contains spaced-apart parallel openings or apertures 54 for admitting a flow of ambient air from the surrounding environment into the dispenser chamber 23 (FIGS. 7 and 8) of dispenser fixture 24. Top wall 52 has a generally cross sectional shape in the form of an arc along its length and presents spaced-apart side wall extensions 26a and 27a, which are connected by an end extension 34a as best shown in FIG. 5. As best shown in FIG. 4 side wall extension 27a is formed with a cooperating component forming hinges 56 that pivotally fasten top wall 52 to the upstanding side wall 27 in order to facilitate movement of top wall 52 relative to dispenser chamber 23 for an opened and closed position of dispenser fixture 24. The top wall 52 overlies the upstanding side walls 26 and 27, the outboard end wall 48, and the inboard end wall 34.

Figure 7:
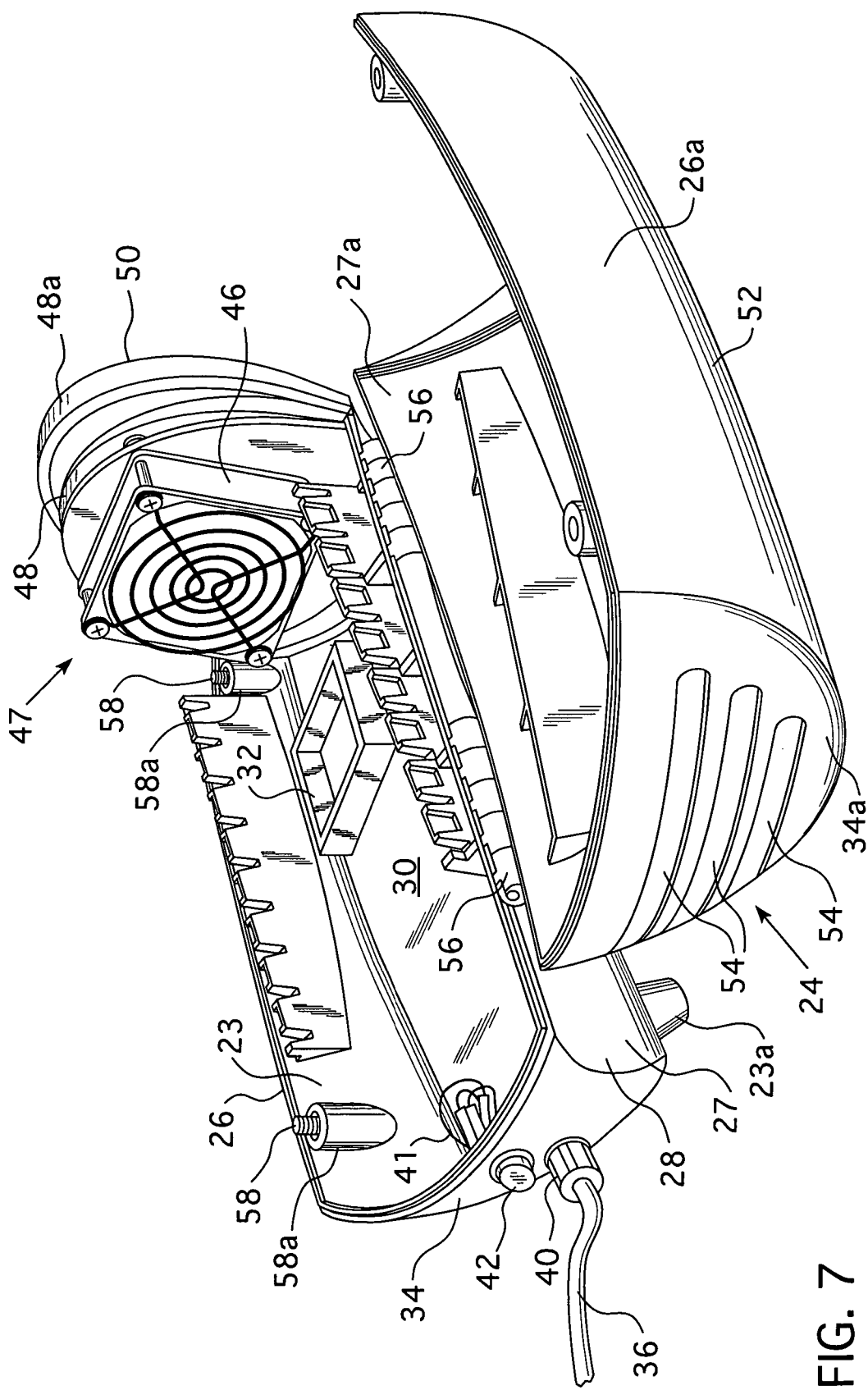
FIG. 7 is a view similar to FIG. 6 with the dispenser fixture orientated in a 180 degree position.

Particularly referring to FIG. 5, in the closed position of dispenser fixture 24, there is defined a condition in which ambient air supplied by the apertures 54 of extension 34a of top wall 52 is enriched with aromatic vapors in the dispenser chamber 23, which vapors are driven by blower 46 as an ambient exhaust. Referring particularly to FIG. 7, the opened position of the dispenser fixture 24, which involves top wall or cover 52 being positioned upward and away from dispenser chamber 23, defines a condition in which the aromatic material is accessible for replacement in the rectangular tray 32 supported by support surface 30 of the elongated dispenser chamber 23. Even though FIG. 7 only shows one tray 32, it is to be appreciated that additional trays 32 may be provided in dispenser chamber 23 and supported by support surface 30.

As best shown in FIGS. 3 and 7, threaded fasteners 58 extend through openings 58a in the upstanding side wall 26 to engage with threads formed in the side wall extension 26a (not shown) for securing side wall extension 26a to upstanding side wall 26 for maintaining dispenser fixture 24 in a closed position.

To enhance the appearance of dispenser fixture 24, the outboard end wall 48 includes an upwardly and outwardly extending extension 48a which joins with an extended part of the top wall 52 to provide an enhanced stream line appearance as best seen in FIGS. 2, 3 and 4.

Figure 9:
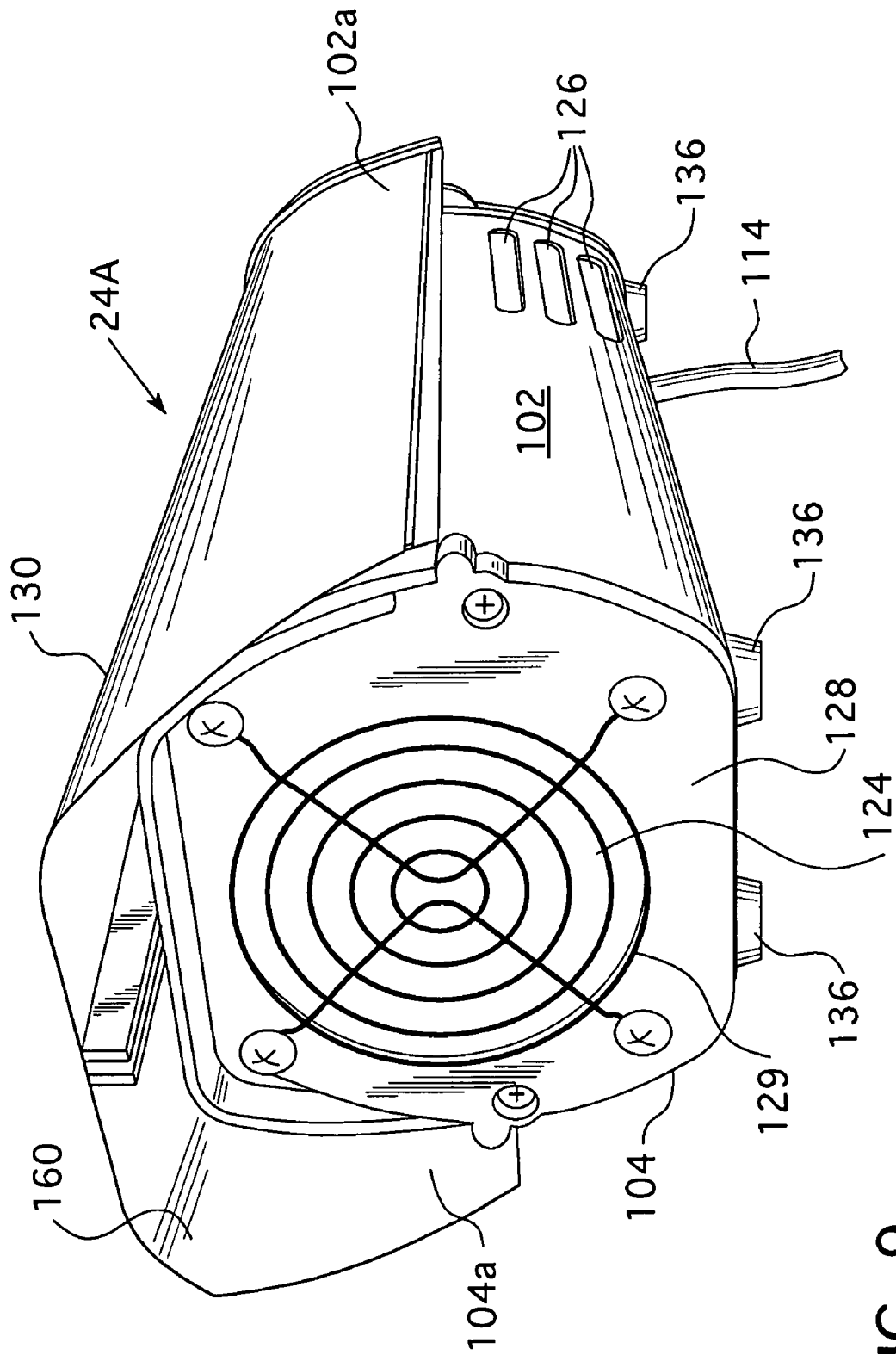
FIG. 9 is a frontal right side isometric view of the dispenser fixture of FIG. 8.
Figure 10:
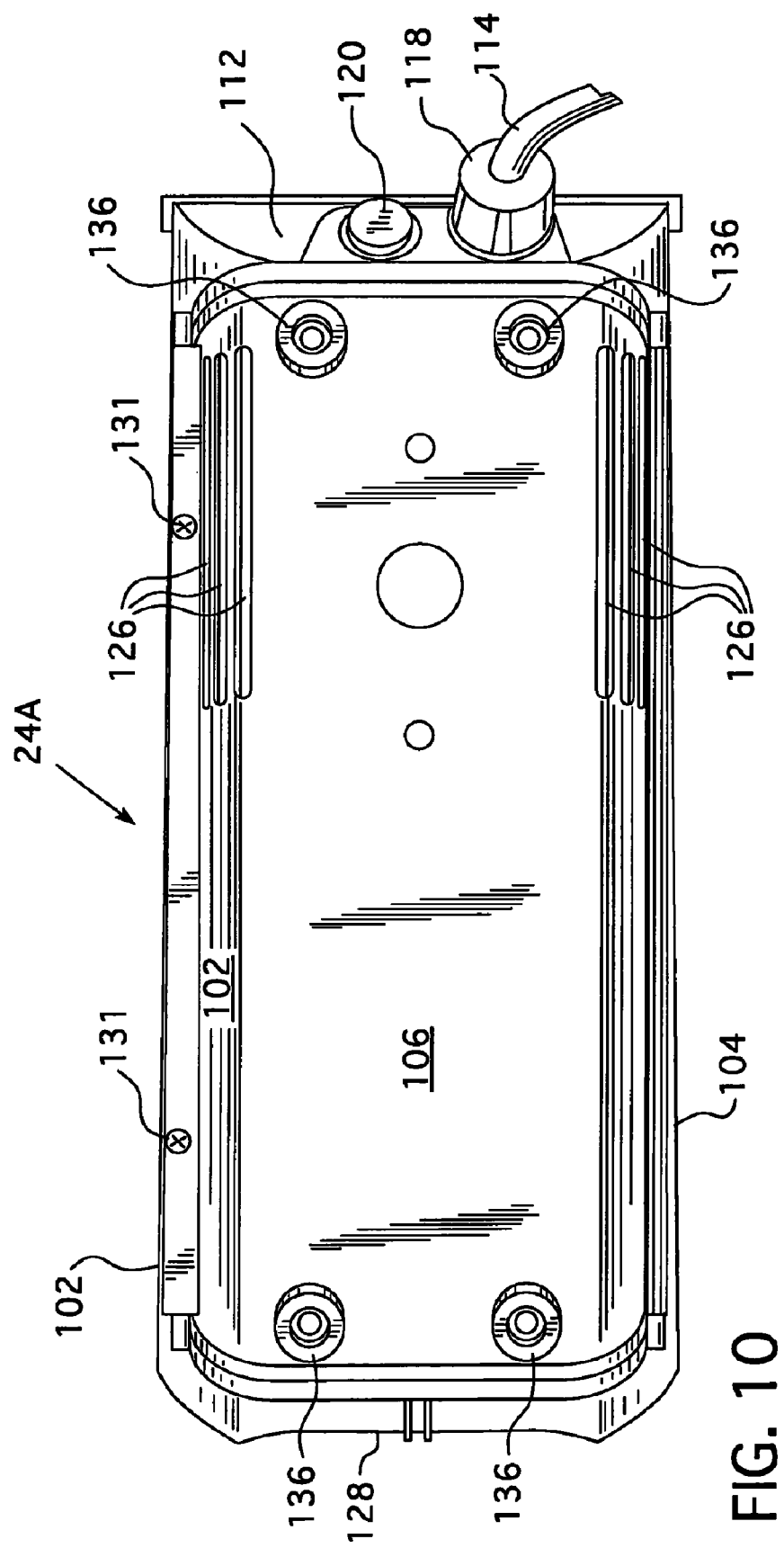
FIG. 10 is a bottom view of the dispenser fixture of FIG. 8.
Figure 11:
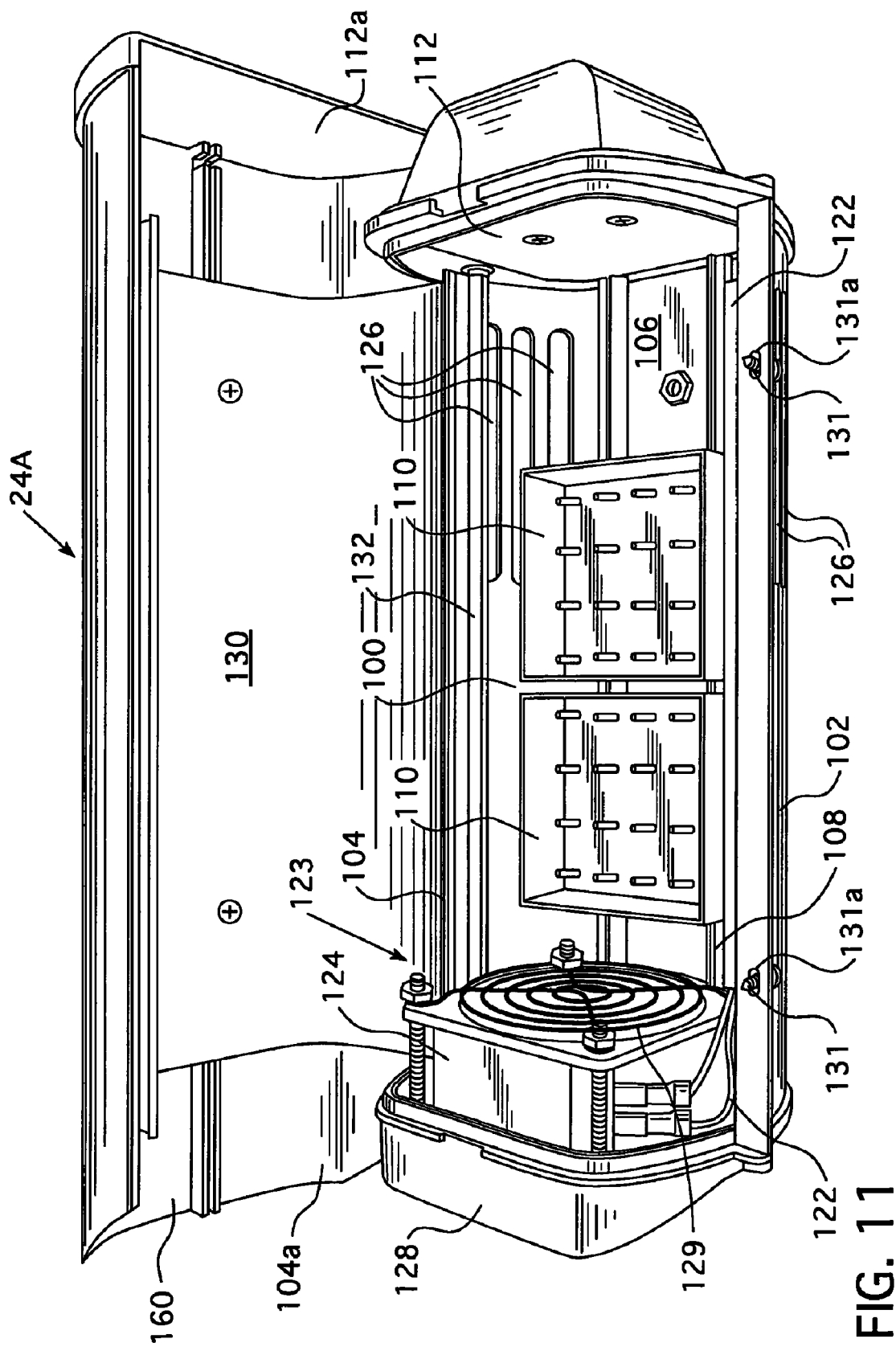
FIG. 11 is an isometric view of the dispenser fixture of FIG. 8 with the top wall or cover pivotally displaced from a closed position.

FIGS. 8-11 illustrate a second embodiment of the present invention involving a dispenser fixture 24A for dispersion of aromatic vapors according to the present invention. As best shown in FIG. 11, dispenser fixture 24A has an elongated dispenser chamber 100 with upstanding side walls 102 and 104 which are joined by a floor wall 106 containing a load bearing surface 108, which receives and supports one or more rectangular trays 110. FIG. 11 shows two such trays 110 which are constructed to contain and support a replaceable supply of aromatic material (not shown).

Figure 8:
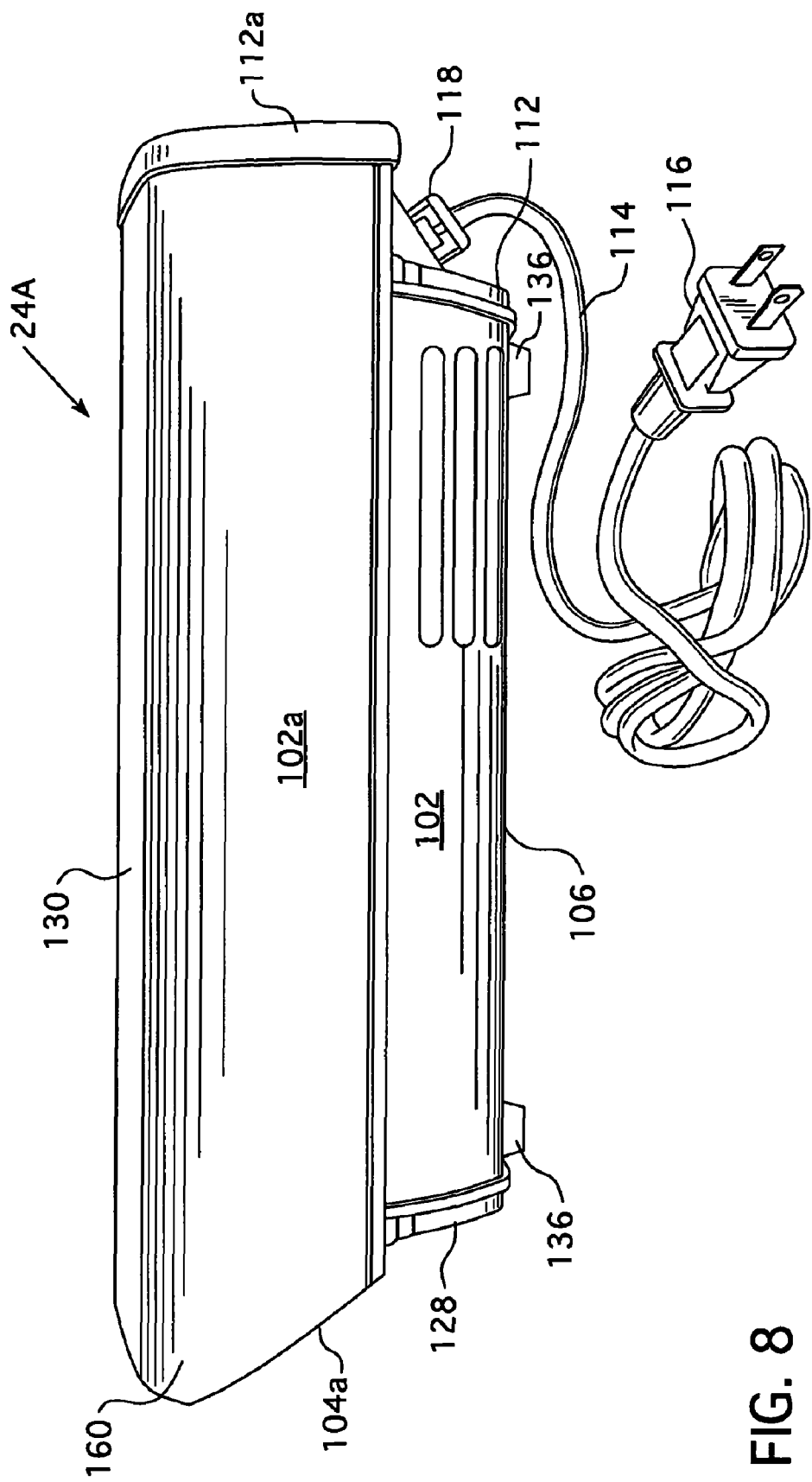
FIG. 8 is a side elevation view of a second embodiment of a dispenser fixture of the present invention.

As best shown in FIG. 8, an inboard end wall 112 supports an electrical supply utility in the form of an electrical utility cable 114 with an outlet plug 116 on its free end and a mounting fixture 118 at its entrance into the interior of the dispenser fixture 24A. As best shown in FIG. 11, suitable wiring within dispenser fixture 24A is arranged to electrically connect a control switch 120 into a circuit for supplying electrical current by feed lines 122 to a blower 124, preferably, in the form of an electric motor, which is mounted in a fan assembly 123. In this embodiment, the upstanding side walls 102 and 104 have a plurality of spaced-apart apertures 126 for allowing a flow of ambient air into the dispenser chamber 100.

Still referring to FIG. 11, blower 124 is mounted to an outboard end wall 128 having an aperture 129 aligned with an air flow path from blower 124. A top wall or cover 130 is formed with a side wall extension 104a. Similar to that of dispenser fixture 24, top wall or cover 130 of dispenser fixture 24A is mounted by one or more hinges (not shown) to upstanding sidewall 104. The hinges pivotally fasten top wall 130 to upstanding side wall 104 in order to facilitate movement of top wall 130 relative to dispenser chamber 100 from an open position to a closed position for dispenser fixture 24A. Top wall 130 overlies each of the upstanding side walls 102 and 104, the inboard end wall 112, and the outboard end wall 128 when the dispenser fixture 24A is in a closed position.

Referring to FIG. 10, in the closed position of dispenser fixture 24A, there is defined a condition in which ambient air supplied by apertures 126 located in sidewalls 102 and 104 is enriched with aromatic vapors in the dispenser chamber 100 and which aromatic vapors are driven by blower 124 as an ambient exhaust. In the opened position of dispenser fixture 24A, a condition exists whereby the aromatic material is accessible for replacement in the elongated dispenser chamber 100.

As shown in FIG. 11, threaded fasteners 131 extend through openings 131a in the upstanding side wall 102 to engage threads (not shown) formed in the side wall extension 102a for securing top wall 130 to sidewall 102 for keeping dispenser fixture 24A closed similar to that of dispenser fixture 24.

As best shown in FIG. 9, the appearance of dispenser fixture 24A of the embodiment of FIGS. 8-11 is enhanced by the formation of a hood-like extension 160 at the top wall 130 which tapers rearward along side wall extensions 102a and 104a to provide an enhanced stream line appearance as best shown in FIG. 9. Referring to FIG. 11, top wall 130 extends downwardly along sidewall extensions 102a and 104a to form an extension 112a for inboard end wall 112. Extension 112a overhangs inboard end wall 112 when dispenser fixture 24A is closed as shown in FIG. 8. It is to be appreciated that when top wall or cover 130 is in the position shown in FIG. 8, that dispenser fixture 24A is closed. Legs 136 support dispenser fixture 24A.

It is to be further appreciated, that even though dispenser fixtures 24 and 24A have legs 23a and 136, respectively, that in accordance with the present invention, these fixtures may be supported by carrier arm 22, which may be mounted to a wall 10 of an establishment or facility F as discussed herein above and as shown in FIG. 1. It is also to be appreciated that dispenser fixtures 24 and 24A may be made of a relatively hard plastic material or metal and that this material in addition to the structure of the dispenser fixtures 24 and 24A provide a robust construction.

While the present invention has been described in connection with the preferred embodiments of the various figures, it is to be understood that other similar embodiments may be used or modifications and additions may be made to the described embodiment for performing the same function of the present invention without deviating there from. Therefore, the present invention should not be limited to any single embodiment, but rather construed in breadth and scope in accordance with the recitation of the appended claims.

The invention claimed is:

1. An elongated dispenser fixture for dispersion of aromatic vapors, comprising:
   an elongated dispenser chamber bounded by a first end wall and a second end wall and extending in a substantially horizontal direction;
   said first end wall containing a fan assembly driven by a motor and including a blower, and an aperture aligned with the air flow path from the blower;
   said second end wall containing fixtures for supplying and controlling electrical current to power said motor of said fan assembly located in said first end wall;
   said elongated dispenser chamber containing at least one receptacle for presenting a supply of aromatic materials to a flow of air passing through apertures positioned in said second end wall and into said elongated dispenser chamber such that a carrier arm supporting the elongated dispenser fixture orientates said motor of said fan assembly located in said first end wall to discharge a stream of air enriched with aromatic vapors out of the aperture in said first end wall in a generally horizontal direction, and
   wherein said apertures in said second end wall, said receptacle for presenting a supply of aromatic materials, said fan assembly, and said aperture in said first end wall are substantially in alignment relative to each other.

2. The elongated dispenser fixture of claim 1 further comprising:
   upstanding side walls joining said first end wall and said second end wall, a floor wall joining said side walls and said end walls, and a top wall overlying said upstanding side walls and said end walls for enclosing said at least one receptacle in said elongated dispenser chamber.

3. The elongated dispenser fixture of claim 1 wherein said elongated dispenser fixture is made of a material selected from the group consisting of a plastic material and a metal material.

4. The elongated dispenser fixture according to claim 1 wherein said elongated dispenser fixture is an electrical device.

* * * * *